(12) United States Patent
Hårdemark

(10) Patent No.: US 10,058,714 B2
(45) Date of Patent: Aug. 28, 2018

(54) METHOD, COMPUTER PROGRAM AND SYSTEM FOR DOSE CALCULATION IN RADIOTHERAPY

(71) Applicant: RaySearch Laboratories AB, Stockholm (SE)

(72) Inventor: Björn Hårdemark, Enskededalen (SE)

(73) Assignee: RaySearch Laboratories AB, Stockholm (SE)

( * ) Notice: Subject to any disclaimer, the term of this patent is extended or adjusted under 35 U.S.C. 154(b) by 0 days.

(21) Appl. No.: 15/515,201

(22) PCT Filed: Mar. 21, 2016

(86) PCT No.: PCT/EP2016/056128
§ 371 (c)(1),
(2) Date: Mar. 29, 2017

(87) PCT Pub. No.: WO2016/156086
PCT Pub. Date: Oct. 6, 2016

(65) Prior Publication Data
US 2017/0225014 A1   Aug. 10, 2017

(30) Foreign Application Priority Data
Mar. 31, 2015 (EP) .................................. 15161820

(51) Int. Cl.
*A61N 5/10* (2006.01)

(52) U.S. Cl.
CPC ........... *A61N 5/1031* (2013.01); *A61N 5/103* (2013.01); *A61N 5/1039* (2013.01)

(58) Field of Classification Search
CPC .. A61N 5/1049; A61N 5/1067; A61N 5/1042; A61N 5/1037; A61N 2005/1055; A61N 5/103; A61N 5/1048; A61N 5/1038; A61N 5/1031; A61N 5/1077; A61N 5/1065; A61N 5/1039; A61N 5/1064;
(Continued)

(56) References Cited

U.S. PATENT DOCUMENTS

| | | | |
|---|---|---|---|
| 2005/0201516 A1* | 9/2005 | Ruchala | A61N 5/103 378/65 |
| 2008/0091388 A1* | 4/2008 | Failla | A61N 5/1031 703/2 |
| 2011/0019889 A1 | 1/2011 | Gering et al. | |

FOREIGN PATENT DOCUMENTS

| | | |
|---|---|---|
| EP | 1 778 353 B1 | 9/2012 |
| WO | WO2006/018761 A1 | 2/2006 |

(Continued)

OTHER PUBLICATIONS

S. Petit et al., "Dose recalculation in megavoltage cone-beam CT for treatment evaluation: Removal of cupping and truncation artefacts in scans of the thorax and abdomen," Radiotherapy and Oncology, vol. 94, 2010, pp. 359-366.

C. Veiga et al., "Toward adaptive radiotherapy for head and neck patients: Feasability study on using CT-to-CBCT deformable registration for "dose of the day" calculations," Med. Phys., vol. 41, No. 3, Mar. 2014, pp. 031703-1 through 031703-12.

*Primary Examiner* — Christine H Matthews
*Assistant Examiner* — Joshua D Lannu
(74) *Attorney, Agent, or Firm* — Drinker Biddle & Reath LLP

(57) ABSTRACT

A method and computer program for dose calculation include using information from a fraction image to update contour information from a planning image and also includes using density information from the fraction image and the planning image for performing dose calculation.

13 Claims, 1 Drawing Sheet

(58) Field of Classification Search
CPC .. A61N 5/1069; A61N 5/1071; A61N 5/1081; A61N 5/1045; A61N 5/107; A61N 2005/1072; A61N 5/1075; A61N 2005/1054; A61N 2005/1061; A61N 5/10; A61N 5/1001; A61N 2005/1074; A61N 2005/1098; A61N 5/062; A61N 2005/1034; A61N 2005/1022; A61N 2005/1041; A61N 2005/1052; A61N 2005/1076; A61N 2005/1087; A61N 5/1047; A61N 5/1084; G06T 11/005; G06T 2207/10081; G06T 2200/04; G06T 2207/20104; G06T 2207/20116; G06T 2207/30096; G06T 7/0083; G06T 7/12; G06T 7/149; G06T 11/003; G06T 2207/10012; G06T 2207/10016; G06T 2207/10076; G06T 2207/10088; G06T 2207/20016; G06T 2207/30016; G06T 2207/30068; G06T 7/11; G06T 7/33

See application file for complete search history.

(56) References Cited

FOREIGN PATENT DOCUMENTS

WO   WO-2014/096993 A1   6/2014
WO   WO 2014096993 A1 *  6/2014   ........... A61N 5/1048

* cited by examiner

METHOD, COMPUTER PROGRAM AND SYSTEM FOR DOSE CALCULATION IN RADIOTHERAPY

This application is the National Stage of International Application No. PCT/EP2016/056128, filed Mar. 21, 2016, and claims benefit of European Patent Application No. 15161820.4 filed Mar. 31, 2015.

TECHNICAL FIELD

The present invention relates to radiotherapy treatment and in particular dose calculation which may be used for example in the optimization of dose planning in radiotherapy.

BACKGROUND AND RELATED ART

Radiotherapy involves subjecting a target, such as a tumor, within a patient to one or more radiation beams. Ideally, a specific dose should be delivered to the target and minimal radiation should reach the surrounding tissue. In particular, the radiation to critical tissues or organs, such as the heart, should be minimized. Normally the radiotherapy is distributed in a number of sessions, for example once a day for a number of days or weeks.

For planning the radiotherapy overall, a 3D planning image of the relevant part of the patient is generated and segmented. Segmenting the image means determining the boundaries of various regions of interest, such as the target and surrounding tissue, organs etc. and entering these boundaries into the image. The planning image may also be based on an image from an image atlas. Since the size and shape of a tumor, and other organs, and their location, will usually change over the course of the radiotherapy, it is common practice to take a fraction image at one or more times during the radiotherapy, for example, at the start of each radiotherapy session. Information from the fraction images is used to update the radiotherapy treatment plan. This is referred to as adaptive radiotherapy treatment planning.

Dose planning requires information about the location of the various organs and also about their material properties, such as density and/or atomic composition. Density information is used for dose planning. If photon radiotherapy is used, the density and atomic composition determine the attenuation of the radiation. If ion radiotherapy such as proton radiotherapy is used, the density and atomic composition determine the stopping power, which affects the distance that the ions will travel within the patient's body. For the initial planning, this information is taken from the planning image. The fraction images are typically used to determine the new boundaries of the regions of interest, to aim the radiation beams correctly.

Therefore, the planning image should comprise information not only about the contours but also about the material properties of each region of interest. As the geometry of the tumor and other tissues changes during the course of therapy, the fraction images are used to obtain up-to-date contour information. Therefore, the fraction images may have considerably less information than the planning images. This is advantageous because it allows for a lower radiation dose to the patient for each fraction image and also for the use of less expensive imaging systems for taking the fraction images. For example a fan beam CT scan (referred to in this document as CT) may be used for the planning image while Cone Beam CT (CBCT) scans are used for the treatment images. CT images comprise all the information needed for dose planning but are relatively expensive and involve a higher radiation dose to the patient than for example CBCT. CBCT on the other hand does not always provide reliable information about material properties and in particular is subject to distortion such as cupping distortion, where the intensity of the image is misrepresented near the edges of the image. Other imaging technologies involve even less or no radiation but do not provide all the information necessary for proper treatment planning.

In adaptive treatment planning, the process of establishing a mapping of coordinates between the planning image and one or more fraction images is called image registration. Several registration methods are known in the art. Particularly preferred are deformable image registration methods, which take into account both the individual motion of each organ, and the deformation that typically occurs during radiotherapy. In deformable registration, each voxel in the planning image is mapped to a corresponding voxel in the fraction image, so that the movement of the corresponding part of the body can be determined. The terms deformable registration and elastic registration are used interchangeably.

European Patent application EP 1 778 353 discloses the use of deformable registration for adapting a radiotherapy plan between the treatment sessions. Contour information is obtained in the fraction images by utilizing deformable registration with the planning image and used to update the radiotherapy plan.

For most of the regions of interest the density varies very little over the course of the radiotherapy. For others, the density may vary significantly within short time frames. For example the size and content of the bowel and the urinary bladder will vary with time. The presence of air or liquid will affect the density, and therefore the attenuation or stopping power of the organ, significantly. Currently available methods for image registration do not account for these changes.

SUMMARY OF THE INVENTION

It is therefore an object of the invention to provide a dose calculation method that will take into account variations in tissue density that may occur over the course of radiotherapy treatment.

This object is achieved according to the invention by a method according to claim 1 and a computer program product according to claim 11. The invention also relates to a system for dose calculation including in a program memory a computer program product according to the invention.

Hence, dose planning may be performed based on up-to-date location information from the fraction image, as is common in the art. The location information may include information about the size, position and contours of organs or tissues in the patient's body. According to the invention the dose planning may also take into account that in some cases the fraction images will have more correct material property information than the planning image in some regions of the image. On the other hand, and as previously mentioned, the planning image may have more correct material property information in some other regions. Therefore, according to the invention, material property information may be taken from both the fraction image and the planning image, or from information related to each of these images, instead of relying only on the planning image for material property information. Preferably, different regions of the images are defined and it is determined that some regions should use material property information from the planning image and others should use material property information from the fraction image. The material property information of a voxel or region typically includes the density and may also include the atomic composition of the region.

According to one embodiment the step of performing dose calculation comprises a. creating a composite basis for calculation, based on the first basis for calculation and the second basis for calculation, the creating comprising
b. determining at least a first area of the composite basis for calculation that is to incorporate material property information based on the second basis for calculation,
c. producing the composite basis for calculation comprising material property information based on the second basis for calculation in the first area and material property information based on the first basis for calculation in at least a second area.

This may involve actually creating a composite image based on the composite basis for calculation. It may also involve creating a data set representing the composite basis for calculation. Alternatively the composite basis for calculation may comprise the first basis for calculation, the second basis for calculation and information determining, for each region, that material property information should be taken from the first or the second basis for calculation, respectively.

The result of the dose calculation may be used for treatment planning. The method is particularly useful for adaptive treatment planning as defined above. The system and method of the invention may be used independently of the type of radiotherapy provided, but will be particularly useful for ion therapy such as proton therapy or electron therapy, since the density of the tissue directly affects the distance travelled by the ions within the patient body, which determines which parts will be affected by the radiation.

The planning image and fraction image may be obtained from an image memory or may be acquired on site. Typically, the planning image will have been taken at an earlier stage of the radiotherapy while the fraction image will be taken at a point in time close to the registration and to a radiotherapy session. The planning image may also be taken from an image atlas and, preferably, adapted to the individual patient. The registration is preferably performed using a deformable registration method.

It is possible to make general specifications, for each portion of the body or for each condition, of the regions of interest for which density information should be taken from the planning image and from the fraction image, respectively, based on standards for segmentation and for the naming of the various regions. In this case, the selection of which material property information that should be based on the first and second basis of calculation, respectively, may be made automatically. The specification may also be made for an individual patient, or treatment plan.

Typically the material property information in parts of the image where these properties are substantially stable, that is, that they are not expected to vary between the time of initial planning and the time of delivery of the fraction, may be taken from the planning image. On the other hand, information should be taken from the fraction image concerning regions and organs for which the properties can change significantly in the time period between the initial planning and the delivery of the fraction, in such a way that it will affect the radiotherapy. This time period may be anything from a couple of hours to several months. Such regions are, for example, stomach, bowel, urinary bladder, uterus, lungs and tongue. It is also possible to use material property information that is derived from both planning image and fraction image, for example as a weighted average of corresponding voxels in the two images. Typically, the material property includes the density of the region of interest, but other properties such as atomic composition may be used instead or in addition.

In a preferred embodiment the planning image is a fan beam CT image and the fraction image is a CBCT image. It is also possible to use other imaging technologies, for example to use an MR image for the planning image and a CBCT image for the fraction image. Preferably a deformable registration method is used for registering the images as this will enable adaptation to any geometrical change that has occurred in the tissues and organs.

BRIEF DESCRIPTION OF THE DRAWINGS

The invention will be described in more detail in the following by way of example only and with reference to the appended drawings, in which.

DETAILED DESCRIPTION OF PREFERRED EMBODIMENTS

Figure 1:
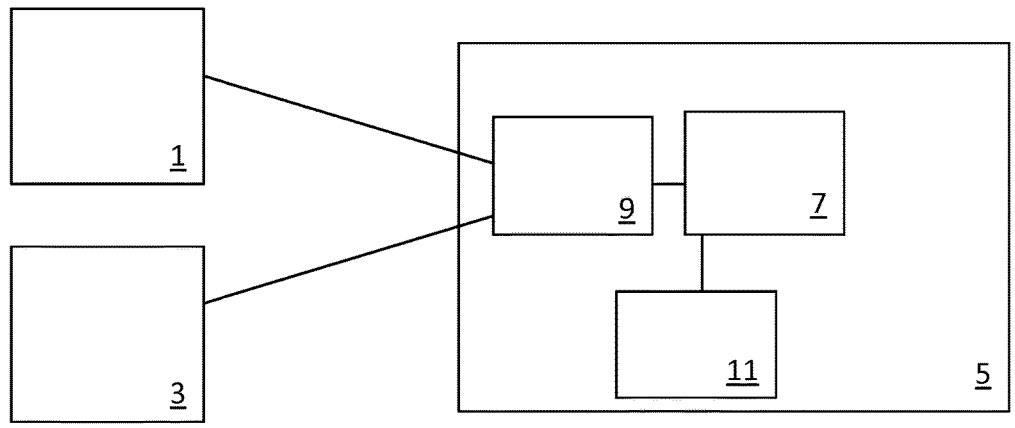
FIG. 1 illustrates a system in which the inventive method may be applied.

FIG. 1 illustrates schematically an embodiment of a system in which the method according to the invention may be performed. The system comprises a first imaging apparatus 1 for acquiring data for producing a planning image which is suitable as a starting point for creating an initial radiotherapy treatment plan. Such imaging apparatuses are well known in the art and will not be discussed in any detail here. The system also comprises a second imaging apparatus 3, for acquiring data for producing a fraction image which is suitable for registering with the planning image for updating the radiotherapy treatment plan. In the context of the invention the first imaging apparatus is typically but not necessarily a CT imaging apparatus and the second imaging apparatus may be a CBCT imaging apparatus. Other types of imaging apparatus may be used, as will be discussed below. Also the planning image may be taken from another source, such as an image atlas.

The first 1 and the second imaging apparatus 3 are connected to a computer 5, arranged to update a radiotherapy treatment plan to create an updated treatment plan based on the initial radiotherapy treatment plan, using information from the planning image and the fraction image. The computer 5 may be the same processor as the one used to determine the initial radiotherapy treatment plan according to algorithms well known in the art, or the initial plan may be provided in some other way. For performing the updating, the computer 5 comprises processing means 7 which will be discussed in more detail below. The computer 5 also comprises data memory 9 and program memory 11. The data memory 9 is arranged to hold at least the following for use by the processor 7: the planning image, the fraction image, and the initial radiotherapy treatment plan. The adaptation of the plan may be performed online or offline, that is, the fraction image taken at fraction n may be used for planning before the same fraction (fraction n), or for planning before the next fraction (fraction n+1) respectively.

In addition the data memory 9 preferably holds information identifying parts of the image in which material property information should be taken from the planning image and from the fraction image, respectively. Alternatively, this may be controlled directly from the computer program, or the information may be entered manually or provided in some other way. How to implement this will be discussed in more detail below. There may also be regions in which material property information should be based on data from both the planning image and the fraction image, as will be discussed in more detail below. The program memory 11 is arranged to hold the computer program for controlling the updating of the initial radiotherapy treatment plan to produce an updated treatment plan.

It should be noted that although the imaging systems 1, 3 and the computer 5 are shown in FIG. 1 as parts of a system, they do not have to be placed in the same location or integrated with each other in any way, except to make the planning image and the fraction image or images available to the computer. This can be achieved in any manner known in the art, including wired or wireless connections, or by use of mobile memory units.

Figure 2:
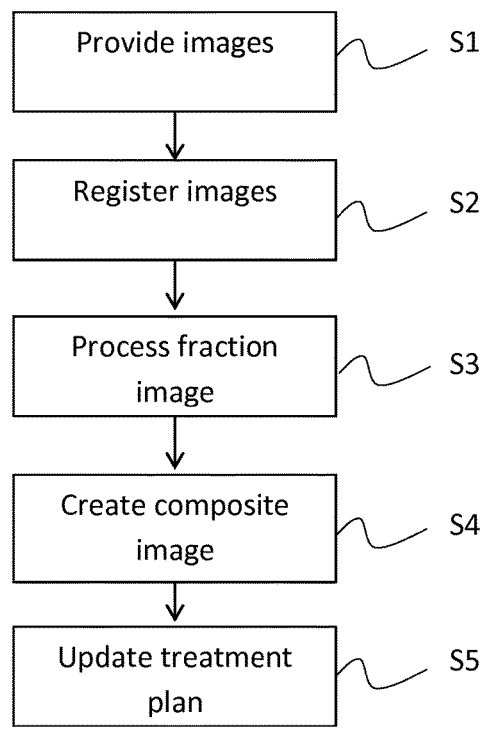
FIG. 2 is a flow chart of a method according to a preferred embodiment of the invention.

FIG. 2 is a flow chart of a method of updating the treatment plan according to one embodiment of the invention. In a first step S1 the planning image and the fraction image are obtained, from the respective imaging system 1, 3 or from a memory in the computer 5. Typically, the planning and fraction images have been taken at different times, using the two different imaging systems, respectively, and entered into the data memory 9. One or both images may also be provided directly from the respective imaging apparatus or from some other source. The planning image has preferably been segmented beforehand, to identify the different organs, tissues etc. in the image. Typically, at least the area that is to be treated, that is, the tumor, is identified by segmentation.

In a step S2 the planning image and the fraction image are registered with each other using a registration method known in the art. Image registration as such is known in the art and means defining the displacement of the elements of one image necessary to map them to the corresponding elements in the other image. Preferably, a deformable registration method is used, which may be used to account for any type of change that may occur to position, size or shape of different organs. The result is a displacement map representing the deformation that must be made to one of the images to match it to the other image. In the context of the invention, preferably the deformation of the planning image needed for registration with the fraction image will be used as a first basis for dose calculation in subsequent steps.

In step S3 a second basis for dose calculation is determined based on the fraction image, comprising both location information and material property information. How to do this is well known to the skilled person.

In step S4 the first basis for dose calculation obtained in step S2 and the second basis for dose calculation obtained in step S3 are used as input data to dose calculation. In its most elaborate form this would involve creating a composite image where some parts are based on the first basis for dose calculation, that is, on the deformed planning image, and some parts are based on the second basis for dose calculation, that is, on information obtained from the fraction image. Instead of actually creating the image, a composite basis for dose calculation may be created, comprising the data for each voxel, taken from the first or second basis for dose calculation according to selection criteria that will be discussed below. It would also be possible to keep the first and second bases for dose calculation and take input from the appropriate one for each voxel when performing the dose calculation. Which basis for dose calculation to use for material property information for which parts of the image is determined based on the segmentation of the images. As mentioned above, segmentation involves determining the boundaries of organs or other regions in the image.

Based on the segmentation it is possible to set the selection criteria to determine one or more organs or regions for which property information should be taken from the first or the second basis for calculation, respectively. This may be selected for each voxel, region or organ individually. In practice, the default for each region or organ may be to use material property information from the first basis of calculation. The regions for which the material property information should be taken from the second basis for calculation must then be indicated. It would of course also be possible to use the second basis of calculation as the default source of material property information and indicate the regions for which the material property information should be taken from the first basis for calculation, or to indicate for each voxel, or region, which basis for calculation to use. The selection may also be controlled manually for an individual case. In a typical case, it may be determined that, for all parts of the image that are within the area identified as, for example, the stomach or the rectum, density information should be taken from the second basis for calculation, that is, based on the fraction image and for all other areas density information should be taken from the deformed the planning image.

Of course, steps S2 and S3 may be performed in arbitrary order. Also, the segmentation may be performed in connection with this method or in a separate procedure.

In an embodiment of step S4, some parts may be taken from the first basis for calculation, and others from the second basis for calculation, whereas for some other parts the material properties should be determined based on both the first and the second bases for calculation. For example, if the default material property information is taken from the first basis of calculation and the second basis of calculation is used for the stomach region, it may be desirable to use an intermediate value in the border area between the stomach and the surrounding tissue. Such an intermediate value may be calculated for each voxel as an average or a weighted average between the values in the planning image and fraction image, respectively. Yet another alternative would be to use a function dependent on the material property value in a particular voxel or region. Such a function might be, for example, "If the density of a particular voxel or group of voxels in the fraction image is lower than a threshold value the density value from the second basis for calculation should be used, otherwise the value from the first basis for calculation should be used". In this example, the values should be based on the second basis for calculation for voxels with a density value below the threshold and on the first basis for calculation for voxels with a density value above the threshold. The threshold value may be for example 0.1 g/cm$^3$, meaning that anything having a lower density is probably air and should be treated like air in the calculations.

In step S5, which is an optional step, the composite basis for dose calculation created in step S4 is used in a procedure where the initial radiotherapy treatment plan is updated, taking into account material property information from the first basis for dose calculation (that is, the planning image) in some areas of the composite image and from the second basis for dose calculation (that is, the fraction image) in other areas of the composite image. As mentioned above it is not necessary to create the composite image.

Later updates may be based on the initial radiotherapy treatment plan, or the updated treatment plan may take the place of the initial radiotherapy treatment plan.

It will also be possible to use information from more than two images to produce the composite image. For example, information from fraction images taken at different times could be applied to the planning image before registration. Alternatively, fraction images could be obtained using different imaging technology to provide optimized information from each of the images in dependence of the properties of each image to take advantage of the different properties of different imaging technologies. In this case step S3 above should be performed for each of the two or more fraction images to create an instance of a second basis for calculation for each of the fraction images. The composite image could include material property information based on the planning image (first basis for calculation) in some areas, while material property information based on each of the fraction images could be used in one or more other regions of the composite image In an alternative embodiment an MR image is used as the planning image and a CBCT image is used as the fraction image. MR provides useful information about material properties and high resolution and contrast but is subject to geometrical distortion, which means that contours may not be correctly represented. A further drawback of MR is that it may be difficult to distinguish between for instance air and bone. Typically, therefore, if such an undetermined area is located close to the skin it is interpreted as bone whereas further into the body it will be interpreted as air. In the head, however there are several areas comprising air adjacent to bone, which cannot be correctly identified using MR imaging. One option if MR is used for the planning image would be to use information from the planning image for the central portions of the image and the treatment image for the information about the contours of the patient and for areas comprising bone and/or air.

The invention claimed is:

1. A method of dose calculation for radiotherapy, comprising:
   a. providing a planning image of a portion of a body to be subjected to radiotherapy;
   b. providing a fraction image of the portion of the body, the fraction image and the planning image taken at different times;
   c. registering the planning image with the fraction image to produce a deformation field for the planning image, and using the deformation field to obtain a first basis for calculation comprising first location information and first material property information related to the portion;
   d. obtaining a second basis for calculation based on the fraction image, comprising second location information and second material property information related to the portion; and
   e. performing dose calculation using both the first basis for calculation and the second basis for calculation and using material property information from the first and the second basis for calculation.

2. The method according to claim 1, wherein the dose calculation is performed using the first material property information from the first basis for calculation in at least a first region of the portion of the body and the second material property information from the second basis for calculation in at least a second region of the portion of the body.

3. The method according to claim 1, wherein the step of performing dose calculation comprises:
   f. producing a composite basis for calculation, based on the first basis for calculation and the second basis for calculation, the producing comprising:
   g. determining at least a first area of the composite basis for calculation that is to incorporate the second material property information based on the second basis for calculation; and
   h. producing the composite basis for calculation comprising the second material property information based on the second basis for calculation in the first area and the first material property information based on the first basis for calculation in at least a second area.

4. The method according to claim 3, wherein the step of producing the composite basis for calculation is performed using material property information from both the fraction image and the planning image in the first area.

5. The method according to claim 3, wherein third material property information in the first area is calculated in at least one voxel using combined second material property information and first material property information from the fraction image and the planning image, respectively.

6. The method according to claim 3, wherein the first area includes at least part of one of the following: stomach, bowel, urinary bladder, uterus, lung, and tongue.

7. The method according to claim 1, wherein the registration is performed using a deformable registration method.

8. The method according to claim 1, wherein the material property information includes density or atomic structure of a region of interest.

9. The method according to claim 1, wherein the planning image is acquired using fan beam CT.

10. The method according to claim 1, wherein the fraction image is acquired using cone beam CT.

11. A non-transient computer readable medium containing program instructions which, when run in a computer will cause the computer to perform the method according to claim 1.

12. A carrier comprising the non-transient computer readable medium of claim 11.

13. A computer system for performing dose calculations for radiotherapy, the system comprising processing means for performing registration of images, said computer system having a memory having stored therein program instructions which, when executed, controls the processing means according to the method of claim 1.

* * * * *